United States Patent
Fernando et al.

(10) Patent No.: US 10,555,555 B2
(45) Date of Patent: Feb. 11, 2020

(54) AEROSOL-GENERATING ARTICLE AND ELECTRICALLY OPERATED SYSTEM INCORPORATING A TAGGANT

(71) Applicant: PHILIP MORRIS PRODUCTS S.A., Neuchatel (CH)

(72) Inventors: Felix Fernando, Old Basing (GB); Dominique Bernauer, Neuchatel (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 615 days.

(21) Appl. No.: 15/101,311

(22) PCT Filed: Dec. 3, 2014

(86) PCT No.: PCT/EP2014/076453
§ 371 (c)(1),
(2) Date: Jun. 2, 2016

(87) PCT Pub. No.: WO2015/082560
PCT Pub. Date: Jun. 11, 2015

(65) Prior Publication Data
US 2016/0302488 A1    Oct. 20, 2016

(30) Foreign Application Priority Data
Dec. 3, 2013  (EP) .................... 13195494

(51) Int. Cl.
*A24F 47/00* (2006.01)
*G01N 21/31* (2006.01)
*H02J 7/00* (2006.01)

(52) U.S. Cl.
CPC ........... *A24F 47/008* (2013.01); *G01N 21/31* (2013.01); *H02J 7/0042* (2013.01)

(58) Field of Classification Search
CPC ....... A24F 47/008; G01N 21/31; H02J 7/0042
(Continued)

(56) References Cited

U.S. PATENT DOCUMENTS

| 5,060,671 A | 10/1991 | Counts et al. |
| 5,388,594 A | 2/1995 | Counts et al. |

(Continued)

FOREIGN PATENT DOCUMENTS

| CN | 102264251 A | 11/2011 |
| CN | 103237468 A | 8/2013 |

(Continued)

OTHER PUBLICATIONS

Japanese Office Action dated Nov. 1, 2018 in corresponding Japanese Patent Application No. 2016-530146, (8 pages).
(Continued)

*Primary Examiner* — Dana Ross
*Assistant Examiner* — Joe E Mills, Jr.
(74) *Attorney, Agent, or Firm* — Oblon, McClelland, Maier & Neustadt, L.L.P.

(57) ABSTRACT

A method of controlling an aerosol-generating system, and the associated system, are provided. The system includes an aerosol-generating article and an aerosol-generating device having a detector configured to detect the presence of the article and to distinguish the article from other articles configured for use with the system, based on a spectroscopic signature of a taggant incorporated within a material of the article. The method includes detecting the presence of the article; determining whether the article includes a taggant; comparing the spectroscopic signature of the detected taggant with a look-up table of taggant spectroscopic signatures corresponding to articles configured for use with the system; preventing activation of the device, including preventing the supply of power to a heating element unless the detected taggant spectroscopic signature corresponds to an article configured for use with the system; and activating the device if the detected signature corresponds to the article.

26 Claims, 5 Drawing Sheets

(58) Field of Classification Search
USPC .......................... 131/330, 273; 392/386–406
See application file for complete search history.

(56) References Cited

U.S. PATENT DOCUMENTS

| | | | |
|---|---|---|---|
| 5,396,911 | A | 3/1995 | Casey, III et al. |
| 5,498,855 | A | 3/1996 | Deevi et al. |
| 5,505,214 | A | 4/1996 | Collins et al. |
| 5,514,630 | A | 5/1996 | Willkens et al. |
| 5,591,368 | A | 1/1997 | Fleischhauer et al. |
| 5,613,505 | A | 3/1997 | Campbell et al. |
| 5,692,525 | A | 12/1997 | Counts et al. |
| 5,934,289 | A | 8/1999 | Watkins et al. |
| 5,967,148 | A | 10/1999 | Harris et al. |
| 7,985,590 | B2 | 7/2011 | McNeil |
| 8,025,231 | B2 * | 9/2011 | Allen ................. G07D 7/003 235/383 |
| 2005/0112360 | A1 | 5/2005 | Berger et al. |
| 2010/0163063 | A1 * | 7/2010 | Fernando ............. A24F 7/008 131/184.1 |
| 2010/0304491 | A1 | 12/2010 | McNeil |
| 2012/0302474 | A1 * | 11/2012 | Faenza ................. B07C 5/342 508/296 |
| 2014/0060555 | A1 * | 3/2014 | Chang ................. A24F 7/008 131/329 |
| 2014/0196736 | A1 | 7/2014 | Fernando et al. |

FOREIGN PATENT DOCUMENTS

| | | |
|---|---|---|
| CN | 103281920 A | 9/2013 |
| EP | 0 277 519 A2 | 8/1988 |
| EP | 0 358 002 A2 | 3/1990 |
| EP | 0 358 002 A3 | 3/1990 |
| EP | 0 857 431 A1 | 8/1998 |
| EP | 0 893 071 A1 | 1/1999 |
| EP | 1 128 741 A1 | 9/2001 |
| EP | 1 439 876 A2 | 7/2004 |
| EP | 1 618 803 A1 | 1/2006 |
| EP | 1 736 065 A1 | 12/2006 |
| EP | 1 750 788 A1 | 2/2007 |
| JP | 2002-332414 | 11/2002 |
| JP | 2006-320286 A | 11/2006 |
| JP | 2007-503511 A | 2/2007 |
| JP | 4322936 B2 | 6/2009 |
| JP | 2012-121171 A | 6/2012 |
| JP | 2012-513750 A | 6/2012 |
| KR | 10-0636287 A | 10/2006 |
| WO | WO 98/23171 A1 | 6/1998 |
| WO | 02/068945 A1 | 9/2002 |
| WO | WO 03/095688 A2 | 11/2003 |
| WO | WO 2004/043175 A1 | 5/2004 |
| WO | WO 2005/020194 A1 | 3/2005 |
| WO | WO 2007/024130 A1 | 3/2007 |
| WO | WO 2007/066374 A1 | 6/2007 |
| WO | WO 2007/068952 A1 | 6/2007 |
| WO | WO 2007/131449 A1 | 11/2007 |
| WO | WO 2007/131450 A1 | 11/2007 |
| WO | WO 2010/073122 A1 | 7/2010 |
| WO | WO 2011/160788 A1 | 12/2011 |
| WO | WO 2012/065754 A2 | 5/2012 |
| WO | WO 2012/072790 A1 | 6/2012 |
| WO | WO 2012/085205 A1 | 6/2012 |

OTHER PUBLICATIONS

Combined Office Action and Search Report dated Jul. 6, 2018 in Chinese Patent Application No. 201480062128.9 (submitting English translation only), 6 pages.

Office Action dated Nov. 1, 2018 in corresponding Japanese Patent Application No. 2016-530146, 15 pages (previously filed on Nov. 19, 2018, submitting English translation only).

International Search Report and Written Opinion of the International Searching Authority dated Mar. 18, 2015, in PCT/EP2014/076453 Filed Dec. 3, 2014.

Ontwerp, et al., "Award for Taggant Technology," AIPA News, Active & intelligent Packaging Industry Association, Aug. 8, 2013 (2 pages), XP055115857.

* cited by examiner

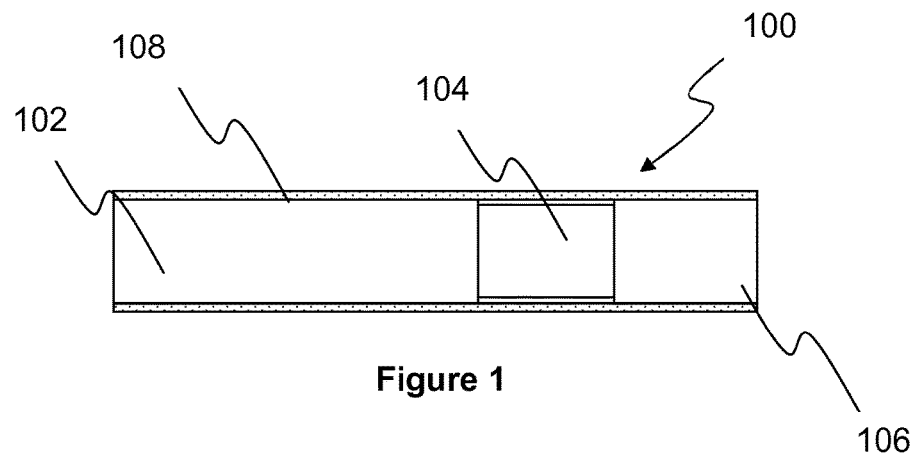
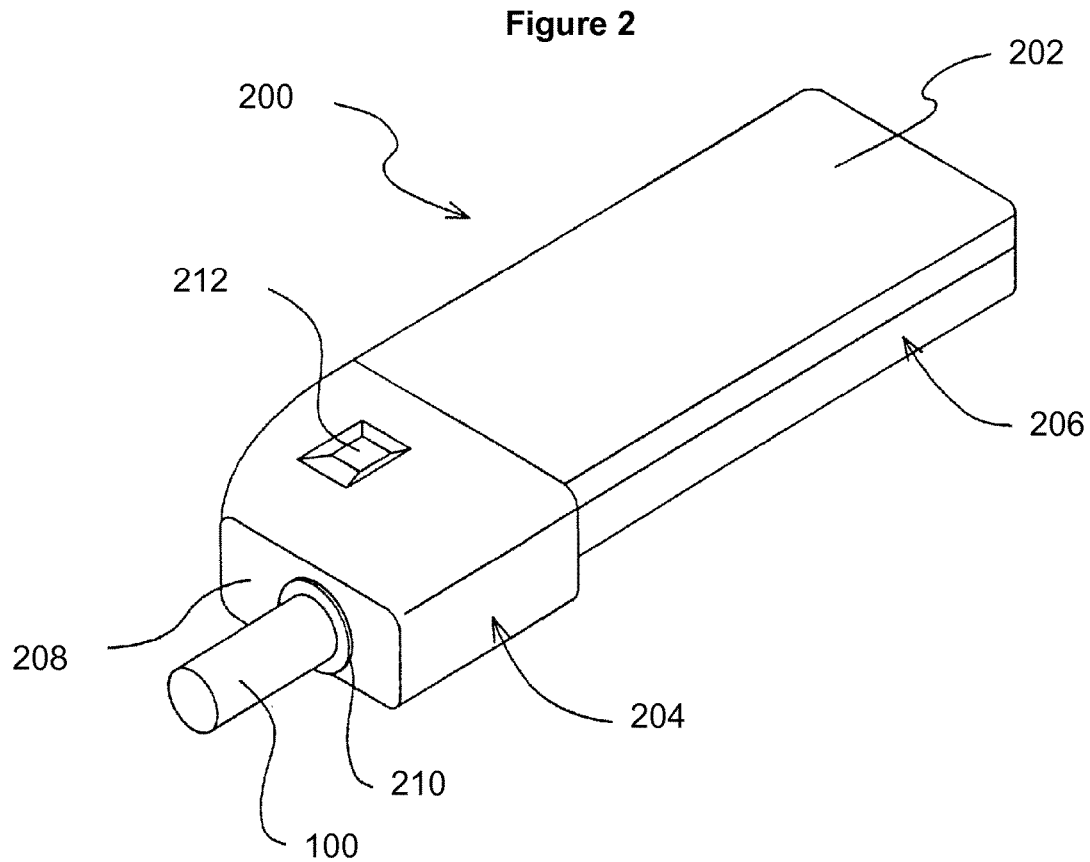

AEROSOL-GENERATING ARTICLE AND ELECTRICALLY OPERATED SYSTEM INCORPORATING A TAGGANT

The present invention relates to an aerosol-generating article incorporating a taggant, for use in an electrically operated aerosol-generating device as part of an electrically operated aerosol-generating system. In particular, the aerosol-generating article may be a smoking article.

A number of documents, for example U.S. Pat. Nos. 5,060,671, 5,388,594, 5,505,214, WO-A-2004/043175, EP-A-1 618 803, EP-A 1 736 065 and WO-A-2007/131449, disclose electrically operated aerosol-generating, smoking, systems, having a number of advantages. One advantage is that they significantly reduce sidestream smoke, while permitting the smoker to selectively suspend and reinitiate smoking.

Electrically heated smoking systems typically include a power supply, such as a battery, connected to a heater to heat an aerosol-forming substrate, to form the aerosol which is provided to the smoker. In operation, these electrically heated smoking systems typically provide a high power pulse to the heater to provide the temperature range desired for operation and to release the volatile compounds. Electrically heated smoking systems may be reusable and may be arranged to receive a disposable smoking article, containing the aerosol-forming substrate, to form the aerosol.

Aerosol-generating, smoking, articles developed for electrically heated smoking systems are typically specially designed, because the flavours are generated and released by a controlled heating of the aerosol-forming substrate, without the combustion that takes place in lit-end cigarettes and other smoking articles. Therefore, the structure of a smoking article designed for an electrically heated smoking system may be different from the structure of a lit-end smoking article. Using a lit-end smoking article with an electrically heated smoking system may result in a poor smoking experience for the user, and may also damage the system because, for example, the smoking article is not compatible with the system. In addition, there may be a number of different smoking articles which are each configured for use with the system, but which each provide a different smoking experience for the user.

Some of the electrically heated smoking systems of the prior art include a detector which is able to detect the presence of a smoking article received in the smoking system. Typically, known systems print identifiable ink on the surface of the smoking article, which is then detected by the electrically heated smoking device. It is an object of the present invention to provide an improved aerosol-generating article, and electrically operated smoking system including a detector which offers additional functionality to the smoker, and increased difficulty to produce counterfeit articles.

According to one aspect of the present invention, there is provided a method of controlling an aerosol-generating system. The system comprises: an aerosol-generating article including at least one component incorporating a taggant having an identifiable spectroscopic signature within a material of the at least one component; and an aerosol-generating device. The aerosol-generating device comprises: a cavity for at least partially receiving the aerosol-generating article; at least one heating element; a power supply for supplying power to the at least one heating element; electrical hardware connected to the power supply and the at least one heating element; and a detector capable of detecting the presence of the aerosol-generating article and distinguishing the aerosol-generating article from other articles configured for use with the aerosol-generating system, based on the spectroscopic signature of the taggant incorporated within a material of the aerosol-generating article. The method comprises the steps of: detecting the presence of an aerosol-generating article; determining whether the aerosol-generating article comprises a taggant; comparing the spectroscopic signature of the detected taggant with a look-up table of taggant spectroscopic signatures corresponding to aerosol-generating articles configured for use with the aerosol-generating system; preventing activation of the aerosol-generating device, including preventing the supply of power to the at least one heating element, unless the detected taggant spectroscopic signature corresponds to an aerosol-generating article configured for use with the aerosol-generating system; and activating the aerosol-generating device if the detected taggant spectroscopic signature corresponds to an aerosol-generating article configured for use with the aerosol-generating system.

Providing such a method of detecting a taggant incorporated into a material of an aerosol-generating article both increases the difficulty of counterfeit articles being produced, reduces the risk that unauthorised aerosol-generating articles are used with the system, and provides the user with a system that is easier to use.

The method preferably further comprises the step of detecting the presence of an aerosol-generating article presented externally to the aerosol-generating device. Providing such functionality enables the user to quickly and easily determine whether an aerosol-generating article is configured for use with the system. To yet further reduce the risk that counterfeit articles, or other articles not configured for use with the system, are used, the step of preventing activation of the aerosol-generating device, may further include preventing the aerosol-generating article from being received in the cavity of the aerosol-generating device. The structural features of the aerosol-generating device to enable the article to be prevented from being received in the cavity are discussed below.

In one embodiment, the aerosol-generating system further comprises a charging unit. In this embodiment, the method further comprises the steps of: detecting the presence of an aerosol-generating article presented externally to the charging unit; and providing an activation signal from the charging unit to the aerosol-generating device unless the detected taggant spectroscopic signature corresponds to an aerosol-generating article configured for use with the aerosol-generating system.

In this embodiment, the charging unit preferably further comprises a cavity for at least partially receiving the aerosol-generating device. The method may further comprise the step of preventing release of the aerosol-generating device from the charging unit unless the detected taggant spectroscopic signature corresponds to an aerosol-generating article configured for use with the aerosol-generating system. Again, such a step yet further reduces the risk that counterfeit articles, or other articles not configured for use with the system, are used. The structural features of the charging unit to prevent the device from being released from the charging unit cavity are discussed below.

The step of activating the aerosol-generating device preferably further includes switching the aerosol-generating device from a standby mode to an active mode. Enabling the device to switch from a standby mode to an active mode allows the device to save power.

Once the device is in use, and power is provided to the at least one heating element to heat the aerosol-generating article and generate an aerosol, the method may further comprise the step of increasing the temperature of the at least one heating element to above a temperature at which the taggant is deactivated, preventing the smoking article from being used again. As will be appreciated, if the taggant is deactivated, it will not be able to be detected by the detector, and thus the device will not be activated and so the article cannot be re-used. This may improve the user experience. The temperature at which the taggant is deactivated may be lower than the operating temperature of the device.

Alternatively, the temperature at which the taggant is deactivated may be higher than the operating temperature of the device. In this alternative, the method may comprise the step of detecting the end of life of the smoking article, and increasing the temperature in dependence on the smoking article having reached the end of its life to a temperature above which the taggant is deactivated.

The end of life of the article may be determined by counting the number of puffs taken by a user, and, or alternatively, timing the length of the puffs taken by a user. The total number of puffs, or the total length of time for the puffs may then be compared to a pre-determined life time for that article.

According to an aspect of the present disclosure, there is provided an aerosol-generating article for use in an electrically operated aerosol-generating device, the article comprising: at least one component incorporating a taggant within a material of the at least one component, wherein the taggant comprises an identifiable spectroscopic signature. The aerosol-generating article may be used in the aerosol-generating system when the above described method is carried out.

The use of the taggant incorporated within the material of a component of the article advantageously prevents the taggant from being removed from the component after manufacture. In this way, the tamper resistance, and difficulty of counterfeiting, of the aerosol-generating article was improved.

In use, the aerosol-generating article is received in an electrically operated aerosol-generating device which comprises means for determining the spectroscopic signature of the taggant. The means for determining the spectroscopic signature preferably comprises a light source and a light sensor. The aerosol-generating device is described in more detail below.

The aerosol-generating article may comprise an aerosol-forming substrate, a hollow tubular element, an aerosol cooling element and a mouthpiece arranged sequentially in co-axial alignment and circumscribed by an outer wrapper.

The taggant may be incorporated into any component of the aerosol-generating article, including but not limited to: paper, such as wrapper paper; filters; tipping papers; tobacco; tobacco wraps; coatings; binders; fixations; glues; inks, foams, hollow acetate tubes; wraps; and lacquers. The taggant may be incorporated into the component by either adding it during the manufacture of the material, for example by adding it to a paper slurry or paste before drying, or by painting or spraying it onto the component. Typically, the taggant is incorporated into the component in trace, nano-gram, quantities. For example, where the taggant is sprayed on the surface, the solution being sprayed may incorporate the taggant in a concentration of between 1 ppm and 1000 ppm.

To enable the taggant to be identified more accurately, the taggant may comprise an identifiable spectroscopic signature in absorption. When the taggant is illuminated by the light source of the aerosol-generating device, the taggant will absorb a specific wavelength, or set of wavelengths, and the wavelengths of light subsequently received by the light sensor will therefore enable the aerosol-generating device to determine the taggant in dependence on the absent wavelengths.

The physical and chemical structure of the taggant can be controlled such that the absorbed wavelength of light can be set as required. In a preferred embodiment, the absorbed wavelength of light is not in the visible spectrum. Preferably, the absorbed wavelength is in the Infra-red or Ultraviolet range.

In addition, or instead of the taggant comprising an identifiable spectroscopic signature in absorption, the taggant may comprise an identifiable spectroscopic signature in emission. When the taggant is illuminated by the light source of the aerosol-generating device, the light preferably excites the taggant and emits at least one wavelength of light, shifted from the wavelength of the excitation light. As will be appreciated, this is a form of photoluminescence, and may be phosphorescence, or fluorescence. By controlling the physical and chemical structure of the taggant the spectroscopic signature can be controlled. In some embodiments, the identifiable signature may be in dependence on the time response of the emission in relation to the excitation, or the decay rate of the emission after excitation.

In a preferred embodiment, the wavelength of the emitted light is not in the visible spectrum. Preferably, the wavelength of the emitted light is in the Infra-red or Ultraviolet range.

In a preferred embodiment, the taggant is distributed throughout the material. By distributing the taggant throughout the material the orientation of the aerosol-generating article within the aerosol-generating device is not important. This enables the use of the system to be simpler for the user. In addition, by distributing the taggant throughout the material the tamper resistance of the article is improved, because it is more difficult to completely remove the taggant. In a particularly preferred embodiment, the taggant is substantially homogeneously distributed throughout the material.

There are preferably a plurality of taggants provided for use in the aerosol-generating article, each taggant having a different, and identifiable spectroscopic signature. In this way, a plurality of aerosol-generating articles can be provided, each having a different taggant having a different spectroscopic signature to enable the aerosol-generating device to distinguish between the aerosol-generating articles and operate accordingly. The operation of the aerosol-generating device is described in detail below.

The taggant is preferably stable at elevated temperatures of up to 1500 degrees Celsius. As used herein, the term stable refers to the taggant having a consistent spectroscopic signature, and that the taggant will not decompose. By providing a taggant which remains stable at elevated temperatures standard manufacturing processes may be used when manufacturing the aerosol-generating article, and in manufacturing the material of the aerosol-generating component.

The material of the aerosol-generating component incorporating the taggant may be manufactured by adding the taggant as an ingredient in the slurries used to make the material. The slurries may then be formed, for example by casting, and dried to produce the material, such as paper or wrapper material.

The taggant may be configured such that at normal operating temperature of the aerosol-generating article the taggant is deactivated. As used herein, deactivated refers to the taggant no longer having the identifiable spectroscopic signature. In use, the temperature required to generate an aerosol is greater than the temperature required to deactivate the taggant. In this way, the aerosol-generating device can determine whether the aerosol-generating article has been used previously, and operate accordingly. The temperature range of the aerosol-generating article components during normal operation is preferably between about 50 degrees Celsius and about 300 degrees Celsius depending on the location and type of component of the aerosol-generating device. As such, preferably the taggant is deactivated at a temperature between about 50 degrees Celsius and about 500 degrees Celsius. More preferably, the taggant is deactivated at a temperature between about 70 degrees Celsius and about 100 degrees Celsius.

The taggant may be deactivated by decomposing at the above described elevated temperatures such that is no longer has the identifiable spectroscopic signature. Alternatively, the taggant may be deactivated by being masked by an additional, temperature dependent, additive. The additional additive may become opaque at the elevated temperature, or may change colour to mask the taggant's signature.

Similarly, to the above description of the taggant being stable at elevated temperatures, the taggant is preferably chemically stable. Preferably, the taggant is sufficiently chemically stable so as not to decompose during manufacture of the material or the component. Thus, the taggant is preferably stable when it is: exposed to liquid water; exposed to water vapour; exposed to other commonly used solvents; upon drying; upon physical deformation of the material to form the component; upon exposure to increased temperatures; and upon exposure to reduced temperatures. As such, during the above described material manufacturing process, the taggant does not decompose and the taggant maintains the identifiable spectroscopic signature.

The taggant is preferably in powder form. Taggant powder advantageously enables the taggant to be incorporated into the material more easily. Preferably, the taggant is a powder composed of at least one of: a rare earth; an actinide metal oxide; a ceramic. The rare earth is preferably a lanthanide.

The identifiable spectroscopic signature of the taggant may be associated with the aerosol-generating article type, the aerosol-forming substrate type, the date of production, the place of production, the batch number and other production details, and the use-by-date.

Where the aerosol-generating article comprises an outer wrapper, the outer wrapper, for example, may be a cigarette paper outer wrapper.

The aerosol-generating article may be between about 30 mm and about 120 mm in length, for example about 45 mm in length. The aerosol-generating article may be between about 4 mm and about 15 mm in diameter, for example about 7.2 mm. The aerosol-forming substrate may be between about 3 mm and about 30 mm in length.

As described above, preferably, the aerosol-generating article includes an aerosol-forming substrate. The aerosol-forming substrate preferably comprises a tobacco-containing material containing volatile tobacco flavour compounds which are released from the substrate upon heating. Alternatively, the aerosol-forming substrate may comprise a non-tobacco material such as those used in the devices of EP-A-1 750 788 and EP-A-1 439 876. Preferably, the aerosol-forming substrate further comprises an aerosol former. Examples of suitable aerosol formers are glycerine and propylene glycol. Additional examples of potentially suitable aerosol formers are described in EP-A-0 277 519 and U.S. Pat. No. 5,396,911. The aerosol-forming substrate may be a solid substrate. The solid substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. Optionally, the solid substrate may contain additional tobacco or non-tobacco volatile flavour compounds, to be released upon heating of the substrate.

Optionally, the solid substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, such as those disclosed in U.S. Pat. Nos. 5,505,214, 5,591,368 and 5,388,594, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix. The solid substrate may be deposited on the surface of the carrier in the form of, for example, a sheet, foam, gel or slurry. The solid substrate may be deposited on the entire surface of the carrier, or alternatively, may be deposited in a pattern in order to provide a non-uniform flavour delivery during use. Alternatively, the carrier may be a non-woven fabric or fibre bundle into which tobacco components have been incorporated, such as that described in EP-A-0 857 431. The non-woven fabric or fibre bundle may comprise, for example, carbon fibres, natural cellulose fibres, or cellulose derivative fibres.

The aerosol-forming substrate may be a liquid substrate and the smoking article may comprise means for retaining the liquid substrate. For example, the smoking article may comprise a container, such as that described in EP-A-0 893 071. Alternatively or in addition, the smoking article may comprise a porous carrier material, into which the liquid substrate may be absorbed, as described in WO-A-2007/024130, WO-A-2007/066374, EP-A-1 736 062, WO-A-2007/131449 and WO-A-2007/131450. The aerosol-forming substrate may alternatively be any other sort of substrate, for example, a gas substrate, or any combination of the various types of substrate. The taggant may be incorporated into the means for retaining the liquid substrate, for example within the material forming the container for retaining the liquid substrate. Alternatively or in addition, where present, the taggant may be incorporated into the porous carrier material.

The aerosol-generating article is preferably a smoking article.

According to a further aspect of the present invention, there is provided an electrically operated aerosol-generating system, comprising: an aerosol-generating article including at least one component incorporating a taggant having an identifiable spectroscopic signature within a material of the at least one component. The article and the taggant are preferably as described herein. The system further comprises an aerosol-generating device, comprising: a cavity for at least partially receiving the aerosol-generating article; at least one heating element; a power supply for supplying power to the at least one heating element; electrical hardware connected to the power supply and the at least one heating element; and a detector capable of detecting the presence of the aerosol-generating article and distinguishing the aerosol-generating article from other articles configured for use with the aerosol-generating system, based on the spectroscopic signature of the taggant incorporated within a material of the aerosol-generating article. The electrical hardware is configured to carry out the method of controlling the aerosol-generating system as described above.

The detector may be provided adjacent an external surface of the aerosol-generating device. The detector may be provided at any position along the external surface of a housing of the aerosol-generating device. In one embodiment, the detector is provided at about the mid-point along the length of the housing. Where the detector is provided adjacent an external surface of the aerosol-generating device, the device may further comprise means for preventing the aerosol-article-generating article from being received in the cavity. In this embodiment, the electrical hardware is configured to only allow aerosol-generating articles to be inserted which are configured for use with system. Any suitable means for preventing access to the cavity may be provided, for example, a protrusion may be provided within the cavity which is retracted by the controller when an article configured for use with the system is presented to the detector. Alternatively, a hinge lid which is controlled by the electrical hardware may be provided which at least substantially covers the open end of the cavity. The hinge lid being opened when an article configured for use with the system is presented to the detector.

The aerosol-generating system may further comprise a charging unit. The detector may be provided adjacent an external surface of the charging unit. The detector may be provided at any position along any of the external surfaces the charging unit. In this embodiment, the charging unit comprises electrical hardware configured to provide an activation signal to the aerosol-generating device when the detected taggant spectroscopic signature corresponds to an aerosol-generating article configured for use with the aerosol-generating system. Providing the detector within the charging unit may enable the device to be simpler and may reduce the power consumption of the device.

Furthermore, in the embodiment comprising a detector in the charging unit, the charging unit may further comprise a cavity for at least partially receiving the aerosol-generating device, and means for preventing release of the aerosol-generating device from the charging unit unless the detected taggant spectroscopic signature corresponds to an aerosol-generating article configured for use with the aerosol-generating system. By preventing the device from being released, the user is prevented from using articles not configured for use with the system. Any suitable means for preventing the release may be used. For example, a protrusion, which engages with a corresponding indentation on the device may lock the device within the cavity. The protrusion being movable such that when an article configured for use with the system is presented to the charging unit, the charging unit electrical hardware sends a signal to move the protrusion to release the device. Alternatively, a hinged lid may be provided to cover the open end of the cavity, which is locked until an article configured for use with the system is presented to the charging unit.

According to a further aspect of the present disclosure, there is provided an electrically operated aerosol-generating system. The system comprises: an aerosol-generating article, as described herein, including at least one component incorporating a taggant within a material of the at least one component; a cavity for at least partially receiving the aerosol-generating article; at least one heating element; a power supply for supplying power to the at least one heating element; electrical hardware connected to the power supply and the at least one heating element; and a detector capable of detecting the presence of the aerosol-generating article in the cavity and distinguishing the aerosol-generating article from other articles configured for use with the aerosol-generating system, based on the taggant incorporated within a material of the aerosol-generating article.

As can be seen, the aerosol-generating system is a combination of an aerosol-generating device and one or more aerosol-generating articles for use with the device. The aerosol-generating system may include additional components, such as for example a charging unit for recharging an on-board electric power supply in the electrically operated or electric aerosol-generating device.

The system is preferably arranged to initiate when the detector detects the aerosol-generating article in the cavity. In this way, the user is not required to activate the device using, for example, an activation button.

As described above in relation to the aerosol-generating article, each type of aerosol-generating article is preferably provided with a taggant having a different identifiable spectroscopic signature. The electrical hardware is therefore preferably arranged to establish a heating protocol for the at least one heating element based on the particular aerosol-generating article identified by the detector.

The detector preferably is a spectroscopic detector comprising an optical sensor including at least one light emitter and at least one light sensor. Preferably, the light emitter is configured to emit infra-red wavelength light, or ultraviolet wavelength light. Preferably, the light sensor is configured to detect infra-red wavelength light, or ultraviolet wavelength light.

In one embodiment, the article is one article of a plurality of articles configured for use with the system. In that case, the detector is capable of detecting the presence of the article in the cavity and also capable of distinguishing the article from other of the plurality of articles configured for use with the system, based on the identification information.

In one embodiment, the system is configured to receive a plurality of articles including taggant incorporated thereon, and the system is arranged to operate only with a subset of the plurality of articles configured for use with the system, each article of the subset being identifiable by the detector, based on the taggant properties.

In this way, the system can be set up for use with only particular articles by, for example, programming the electrical hardware. This feature provides a number of advantages. First, this may reduce or eliminate counterfeit smoking articles for use with the system. Second, this may allow manufacturers or distributors to limit the smoking articles which can be used with the system, for example, to account for different smoking articles available in different regions or jurisdictions. Third, this can also allow the smoking system to be configured for use with different subsets of smoking articles. For example, the smoking system, on purchase, might be usable with a first subset of smoking articles. After an update to the electrical hardware, the smoking system might be usable with a second, larger, subset of smoking articles. After a further update to the electrical hardware, the smoking system might be usable with a third, larger, subset of smoking articles.

The aerosol-generating device is preferably a handheld aerosol-generating device that is comfortable for a user to hold between the fingers of a single hand. The aerosol-generating device may be substantially cylindrical in shape. Preferably, the electrically heated smoking system is reusable. Preferably, each article is disposable.

The aerosol-generating device may have a polygonal cross section and a protruding button formed on one face: in this embodiment, the external diameter of the aerosol-generating device may be between about 12.7 mm and about 13.65 mm measured from a flat face to an opposing flat face; between about 13.4 mm and about 14.2 mm measured from an edge to an opposing edge (that is, from the intersection of two faces on one side of the aerosol-generating device to a corresponding intersection on the other side); and between about 14.2 mm and about 15 mm measured from a top of the button to an opposing bottom flat face. The longitudinal length of the device may be between about 70 mm and about 120 mm. The diameter of the device may be between about 10 mm and about 20 mm.

During operation, the aerosol-generating article, and its aerosol-forming substrate, may be completely received in the cavity and thus completely contained within the electrically operated aerosol-generating system. In that case, a user may puff on a mouthpiece of the electrically operated aerosol-generating system. Alternatively, during operation, the article may be partially received in the cavity such that the aerosol-forming substrate is fully or partially contained within the electrically operated aerosol-generating system. In that case, a user may puff directly on the article or on a mouthpiece of the electrically operated aerosol-generating system.

Preferably, and as described above, the electrically operated aerosol-generating system is arranged to initiate, when the detector detects the smoking article in the cavity. The system may be initiated when the electrical hardware connects the power supply and the at least one heating element. Alternatively, or in addition, the system may be initiated when the system switches from a standby mode to an active mode. Alternatively, or in addition, the system may further comprise a switch and may be initiated when the switch is turned on, such that the at least one heating element is heated only when an article is detected in the cavity. Initiation of the system may additionally or alternatively comprise other steps.

The detector is capable of detecting whether or not an aerosol-generating article is present in the cavity, or adjacent the device or charging unit in dependence on the location of the detector. Because of this, the system and smoking article have a number of advantages. For example, power saving is provided, because the system does not need to permanently remain in an active mode, but can remain in a standby mode, switching to the active mode only when an article is detected. In addition, the power used can be optimised for a particular user, when an article is detected, depending on usage habits of the user. The system also allows for a shorter time to first puff for an article, because the article can be heated as soon as it is detected. This minimizes the time delay between a user's first puff and the user receiving the aerosol. Furthermore, safety may be improved because the system activates only when a valid article is detected. Therefore, there is no chance that the heating element will energize unless the valid article is present.

The detector may also be arranged to indicate when the article is removed from the cavity. In that case, the system may be arranged to switch from the active mode to the standby mode. Alternatively, or in addition, if the system comprises a switch, the switch may be turned off when the smoking article is removed from the cavity.

Preferably, the electrical hardware comprises a programmable controller, for example, a microcontroller, for controlling operation of the heating element. In one embodiment, the controller may be programmable by software. Alternatively, the controller may comprise application specific hardware, such as an Application-Specific Integrated-Circuit (ASIC), which may be programmable by customising the logic blocks within the hardware for a particular application. Preferably, the electrical hardware comprises a processor. Additionally, the electrical hardware may comprise memory for storing heating preferences for particular articles, user preferences, user smoking habits or other information. Preferably, the information stored can be updated and replaced depending on the particular articles usable with the smoking system. Also, the information may be downloaded from the system.

In one exemplary embodiment, the electrical hardware comprises a sensor to detect air flow indicative of a user taking a puff. The sensor may comprise a thermistor. The sensor may be an electro-mechanical device. Alternatively, the sensor may be any of: a mechanical device, an optical device, an opto-mechanical device and a micro electro mechanical systems (MEMS) based sensor. In that case, the electrical hardware may be arranged to provide an electric current pulse to the at least one heating element when the sensor senses a user taking a puff. In an alternative embodiment, the system further comprises a manually operable switch, for a user to initiate a puff.

Preferably, the electrical hardware is arranged to establish a heating protocol for the at least one heating element based on the particular article identified by the detector.

The heating protocol may comprise one or more of: a maximum operating temperature for the heating element, a maximum heating time per puff, a minimum time between puffs, a maximum number of puffs per article and a maximum total heating time for the article. Establishing a heating protocol tailored to the particular article is advantageous because the aerosol-forming substrates in particular articles may require, or provide an improved user experience with, particular heating conditions. As already mentioned, preferably, the electrical hardware is programmable, in which case various heating protocols may be stored and updated.

Preferably, the electrical hardware is arranged to store information based on the particular article identified by the detector. This allows monitoring of the various article types used by a particular user, in order to track customer preferences. The information may be stored in the electrical hardware, preferably in the memory. The information is preferably retrievable from the electrical hardware.

The at least one heating element may comprise a single heating element. Alternatively, the at least one heating element may comprise more than one heating element. The heating element or heating elements may be arranged appropriately so as to most effectively heat the aerosol-forming substrate in an article.

The at least one heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Examples of suitable composite heating elements are disclosed in U.S. Pat. No. 5,498,855, WO-A-03/095688 and U.S. Pat. No. 5,514,630.

Alternatively, the at least one heating element may comprise an infra-red heating element, a photonic source such as, for example, those described in U.S. Pat. No. 5,934,289, or an inductive heating element, such as, for example, those described in U.S. Pat. No. 5,613,505.

The at least one heating element may take any suitable form. For example, the at least one heating element may take the form of a heating blade, such as those described in U.S. Pat. Nos. 5,388,594, 5,591,368 and 5,505,214. Alternatively, the at least one heating element may take the form of a casing or substrate having different electro-conductive portions, as described in EP-A-1 128 741, or an electrically resistive metallic tube, as described in WO-A-2007/066374. Alternatively, one or more heating needles or rods that run through the centre of the aerosol-forming substrate, as described in KR-A-100636287 and JP-A-2006320286, may also be suitable. Alternatively, the at least one heating element may be a disk (end) heater or a combination of a disk heater with heating needles or rods. Other alternatives include a heating wire or filament, for example a Ni—Cr, platinum, tungsten or alloy wire, such as those described in EP-A-1 736 065, or a heating plate.

The at least one heating element may heat the aerosol-forming substrate by means of conduction. The heating element may be at least partially in contact with the substrate, or the carrier on which the substrate is deposited. Alternatively, the heat from the heating element may be conducted to the substrate by means of a heat conductive element. Alternatively, the at least one heating element may transfer heat to the incoming ambient air that is drawn through the electrically operated aerosol-generating system during use, which in turn heats the aerosol-forming substrate by convection. The ambient air may be heated before passing through the aerosol-forming substrate, as described in WO-A-2007/066374.

According to a yet further aspect of the present invention, there is provided a method of controlling an aerosol-generating system. The system comprises: an aerosol-generating article including at least one component incorporating a taggant having an identifiable spectroscopic signature within a material of the at least one component; and an aerosol-generating device. The aerosol-generating device comprises: a cavity for at least partially receiving the aerosol-generating article; at least one heating element; a power supply for supplying power to the at least one heating element; electrical hardware connected to the power supply and the at least one heating element; and a detector capable of detecting the presence of the aerosol-generating article and determining the spectroscopic signature of the taggant incorporated within a material of the aerosol-generating article. The method comprises the steps of: in a first mode of operation: detecting the presence of an aerosol-generating article; and switching to a second mode of operation when the presence of an aerosol-generating article is detected; and in the second mode of operation: determining whether the aerosol-generating article comprises a taggant; and if so, determining the spectroscopic signature of the detected taggant.

Preferably, in the first mode the detector operates in a low power mode, and in the second mode, the detector operates in a high power mode.

By operating the system in two distinct modes, the total power consumption of the system may be reduced, which enables the operational time of the system to be increased for a given capacity of power supply. As will be appreciated, alternatively the size of the system may be reduced by reducing the size and therefore capacity of the power supply while maintaining the operational time of the system.

In the first mode, the detector may be configured to detect the presence of an aerosol-generating article by monitoring for a change in the received signal. The method may comprise comparing the received signal to a threshold value, where it is determined that an aerosol-generating article is present if the signal exceeds the threshold. Such a threshold comparison may reduce the rate of false positives, thus further increasing the operational time of the system.

In the first mode, the method may comprise detecting the presence of an aerosol-generating article using a proximity sensor, and in the second mode, the method may comprise determining the spectroscopic signature of the detected taggant using a light emitter and receiver. The proximity sensor may be a capacitive-, photoelectric- or inductive-type proximity sensor. Preferably, the proximity sensor is a capacitive-type sensor. In a particularly preferred embodiment, the capacitive-type sensor is optimised for recognising the paper wrapper of an aerosol-generating article.

The first mode may also use the same light emitter and receiver as used in the second mode. However, the power provided to the light emitter is lower in the first mode of operation than in the second mode of operation. In the first mode, it is only required to determine the presence of an aerosol-generating article which requires less power than when determining the spectroscopic signature of the taggant.

The method according to this yet further aspect of the present invention may also comprise any of the other method steps and features as described herein, where appropriate.

According to a yet further aspect of the present invention, there is provided an electrically operated aerosol-generating system. The system comprises: an aerosol-generating article including at least one component incorporating a taggant having an identifiable spectroscopic signature within a material of the at least one component; and an aerosol-generating device. The aerosol-generating device comprises: a cavity for at least partially receiving the aerosol-generating article; at least one heating element; a power supply for supplying power to the at least one heating element; electrical hardware connected to the power supply and the at least one heating element; and a detector capable of detecting the presence of the aerosol-generating article and determining the spectroscopic signature of the taggant incorporated within a material of the aerosol-generating article. The detector is configured to operate in a first mode, where the detector is configured to detect the presence of an aerosol-generating article, and in a second mode, where the detector is configured to determine whether the aerosol-generating article comprises a taggant, and if so, determine the spectroscopic signature of the detected taggant. The detector is further configured to switch from the first mode of operation to the second mode of operation when the presence of an aerosol-generating article is detected.

In a preferred embodiment, the power consumption of the detector in the first mode of operation is lower than the power consumption of the detector in the second mode of operation. In one embodiment, the power consumption in the first mode is between about 3 mA and about 6 mA, preferably about 5 mA, and the power consumption in the second mode is between about 7 mA and about 10 mA, preferably about 8 mA.

By operating the system in two distinct modes, the total power consumption of the system may be reduced, which enables the operational time of the system to be increased for a given capacity of power supply. As will be appreciated, alternatively the size of the system may be reduced by reducing the size and therefore capacity of the power supply while maintaining the operational time of the system.

The detector may includes a proximity detector, the proximity detector being active in the first mode of operation. Preferably, the proximity detector is not active in the second mode of operation. The proximity detector may be a capacitive-, photoelectric-, or inductive-type capacitive proximity detector.

The electrical hardware may be configured to compare the received signal from the detector, when the detector is operating in the first mode, to a threshold value, where it is determined that an aerosol-generating article is present if the signal exceeds the threshold. Such a threshold comparison may reduce the rate of false positives, thus further increasing the operational time of the system.

The detector of the aerosol-generating device may be a single detector comprising a light emitter and a light detector, where in the first mode, the light emitter operates at a lower power than in the second mode. In the first mode, the light detector is only monitoring for a change in received signal, and so the power requirements are lower.

The electrical hardware may be configured to switch the detector from the first mode of operation to the second mode of operation when the presence of an aerosol-generating article is detected.

The system according to this yet further aspect of the present invention may also comprise any of the other system features, or be configured to carry out any of the method steps as described herein, where appropriate.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention will be further described, by way of example only, with reference to the accompanying drawings in which:

FIG. 1 shows an aerosol-generating article according to the invention;

FIG. 2 shows an aerosol-generating system according to the invention;

Figure 3:
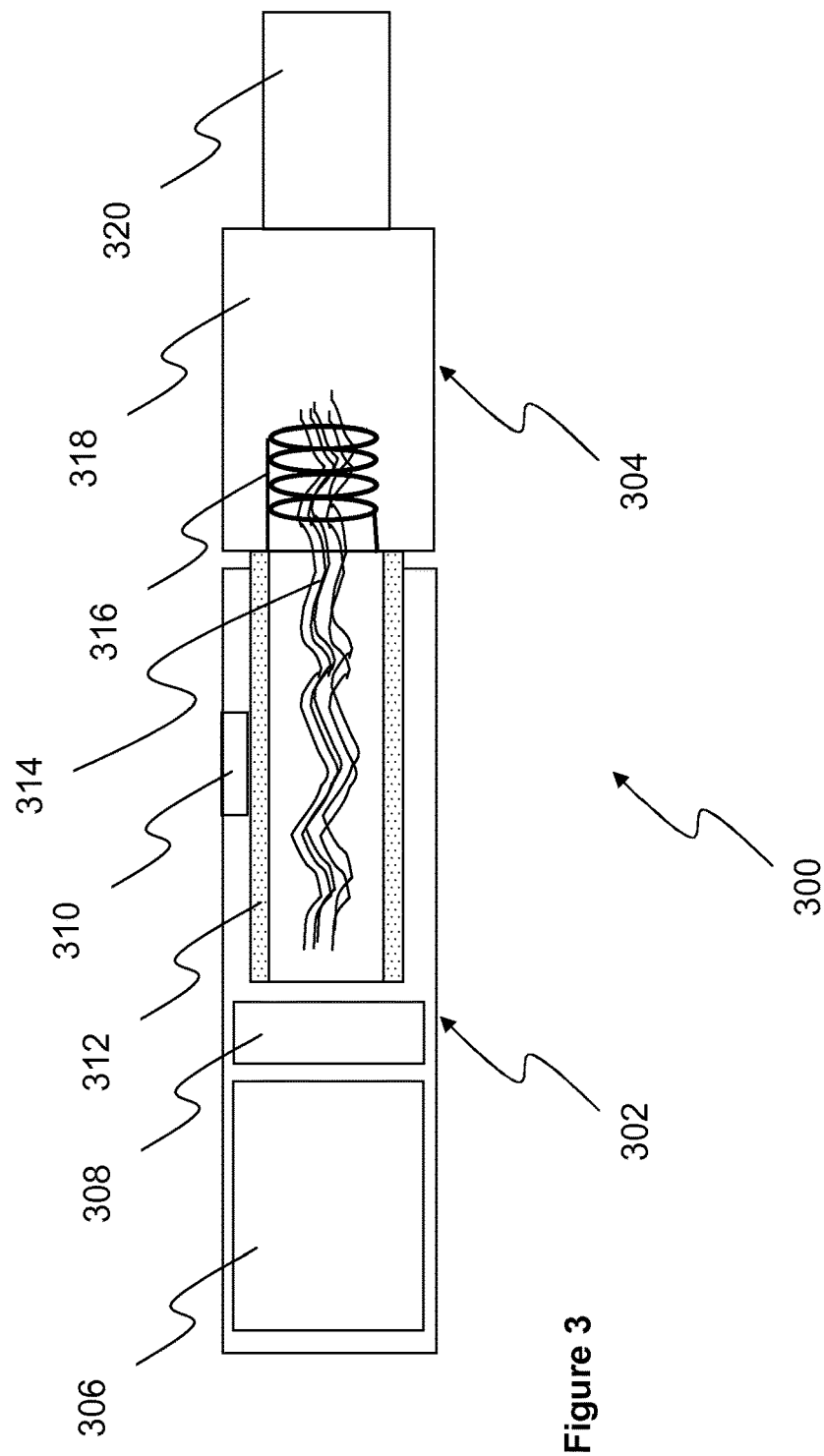
FIG. 3 shows a schematic representation of an alternative aerosol-generating system according to the invention.

FIG. 1 shows an aerosol-generating article 100. The article 100 comprises an aerosol-forming substrate 102, a hollow tubular transfer element 104, a mouthpiece 106, and an outer wrapper 108. The outer wrapper 108 comprises a taggant (represented by the dots). The taggant is incorporated in the wrapper during manufacturing of the material.

The wrapper material in this example is manufactured by incorporating the taggant, in powder form, to the wrapper paper material slurry, before the slurry is formed into paper and dried. The taggant is thermally and chemically stable at the temperature and conditions used during manufacture such that the final material is provided with a taggant. Alternatively, the taggant may be applied to the wrapper material in a solution by spraying, printing, painting or the like.

The aerosol-generating article for use in an electrically operated aerosol-generating device as described below, incorporates the taggant within the wrapper. The taggant has an identifiable spectroscopic signature.

The use of the taggant incorporated within the material of the wrapper prevents the taggant from being removed from the wrapper after manufacture. In this way, the tamper resistance, and difficulty of counterfeiting, of the aerosol-generating article are improved.

The taggant material can be selected to control the optical properties such that it can absorb a specific wavelength of light to enable identification and/or emit light at a shifted wavelength as compared to a wavelength of light used to excite the taggant.

FIG. 2 shows a perspective view of one exemplary embodiment of an electrically operated aerosol-generating system 200 according to the invention. The electrically operated aerosol-generating system 200 is a smoking system comprising a housing 202 having a front housing portion 204 and a rear housing portion 206. The front housing portion 204 includes a front end portion 208 having a cavity 210 capable of receiving an article, such as a smoking article. In FIG. 2, the smoking system 200 is shown with a smoking article in the form of cigarette 100. In this embodiment, the front housing portion 204 also includes a display 212. The display 212 is not shown in detail, but it may comprise any suitable form of display, for example a liquid crystal display (LCD), a light-emitting diode (LED) display or a plasma display panel. In addition, the display may be arranged to show any required information, for example relating to smoking article or cleaning article.

The electrically heated smoking system 200 also includes a detector (not shown in FIG. 2) positioned in or adjacent the cavity 210. The detector is able to detect the presence of an article in the cavity and is also able to identify the various articles which may be usable with the system. The detector comprises means for determining the spectroscopic signature of the taggant. The means for determining the spectroscopic signature comprises a light source and a light sensor.

FIG. 3 shows a schematic representation of a further exemplary embodiment of an aerosol-generating system 300 according to the invention. The aerosol-generating system comprises an aerosol-generating device 302 and an aerosol-generating article 304. The aerosol-generating device 302 comprises a power supply 306, such as a battery, control circuitry 308, and a detector 310. The device 302 is also provided with a cavity for receiving the aerosol-generating article 304. The aerosol-generating article 304 comprises an aerosol-generating liquid substrate container 312, a capillary wick 314, an electrically operated heater 316, an aerosol forming chamber 318 and a mouthpiece 320.

The aerosol-generating article 304 is a cartridge, such as a disposable cartridge, for use in the aerosol-generating device 302. The container of the cartridge comprises a taggant, as described herein, incorporated into the material used to form the container. The taggant has an identifiable spectroscopic signature.

Similarly to the exemplary embodiment shown in FIG. 2, the detector 310 is capable of detecting the presence of the aerosol-generating article 304 in the cavity and distinguishing the aerosol-generating article from other articles configured for use with the aerosol-generating system 302, based on the taggant incorporated within the material of the container 312. As will be appreciated, the taggant may be incorporated into any other component of the aerosol-generating article. The detector 310 comprises a light source and a light sensor for determining the spectroscopic signature of the taggant to identify the aerosol-generating article 304.

In use, when the user inserts the aerosol-generating article 304 into the aerosol-generating device 302 the detector 310 determines the type of aerosol-generating article being inserted by emitting light, and detecting the response received by the light sensor.

When the user draws on the mouthpiece, the control circuitry, in dependence on the type of aerosol-generating article 304 detected, provides power to the heater 316 to generate an aerosol. The power supplied may optimised in accordance with the brand of aerosol-generating article, or in accordance with pre-determined user preferences, and so on. Alternatively, or in addition, if the aerosol-generating article 304 is not recognised by the detector, the control circuitry may prevent power being supplied to the heater 316 to prevent the use of unauthorised aerosol-generating articles.

Figure 4:
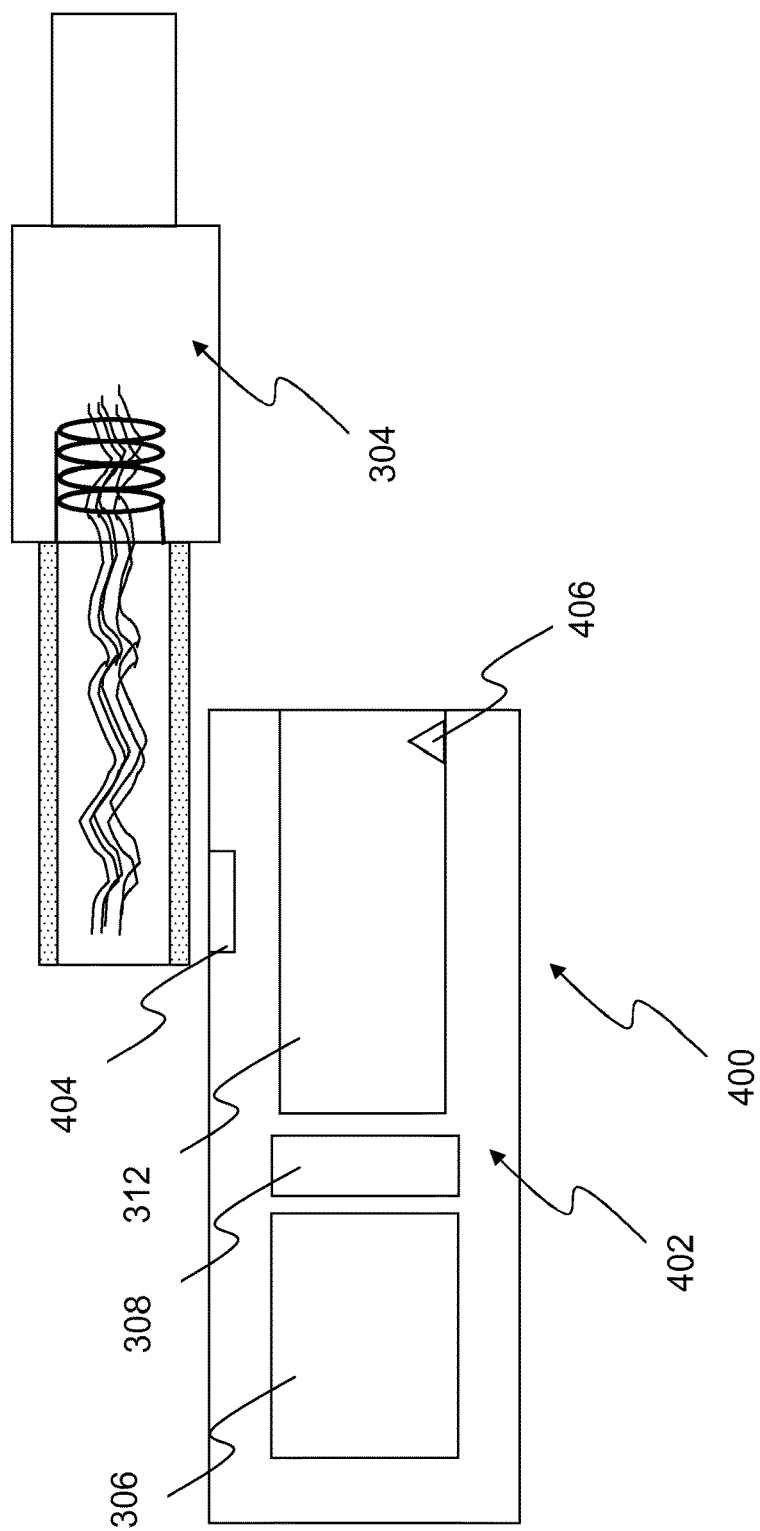
FIG. 4 shows a schematic representation of a further alternative aerosol-generating system according to the invention.

FIG. 4 shows a schematic representation of a further aerosol-generating system 400. The system shown in FIG. 4 is similar to that shown in FIG. 3. The aerosol-generating system 400 comprises an aerosol-generating device 402 and an aerosol-generating article 304; the aerosol-generating article 304 is the same as that described above with reference to FIG. 3. The aerosol-generating device 402 is also the same as described above with reference to FIG. 3, except that the detector 404 is provided on an external surface of the device housing.

In this example, the detector 404 is capable of detecting the presence of the aerosol-generating article 304 being presented externally to the device 402. Again, the detector is capable of distinguishing the aerosol-generating article from other articles configured for use with the aerosol-generating system 400, based on the taggant incorporated within the material of the container 312. As will be appreciated, the taggant may be incorporated into any other component of the aerosol-generating article. The detector 404 comprises a light source and a light sensor for determining the spectroscopic signature of the taggant to identify the aerosol-generating article 304.

As can be seen, the device further comprises a protrusion 406 which when in a first position, as shown, prevents the article 304 from being inserted into the cavity. The protrusion 406 is movable such that in a second position the article 304 may be inserted.

In use, when the user presents the aerosol-generating article 304 to the detector 404, the detector determines the type of aerosol-generating article by emitting light, and detecting the response received by the light sensor.

If the article is configured for use with the system, the control circuitry 308 activates the device, and withdraws the means 406 for preventing the article being inserted into the cavity 312 The user then inserts the article into the cavity and operates the device as described above.

Figures 5A, 5B:
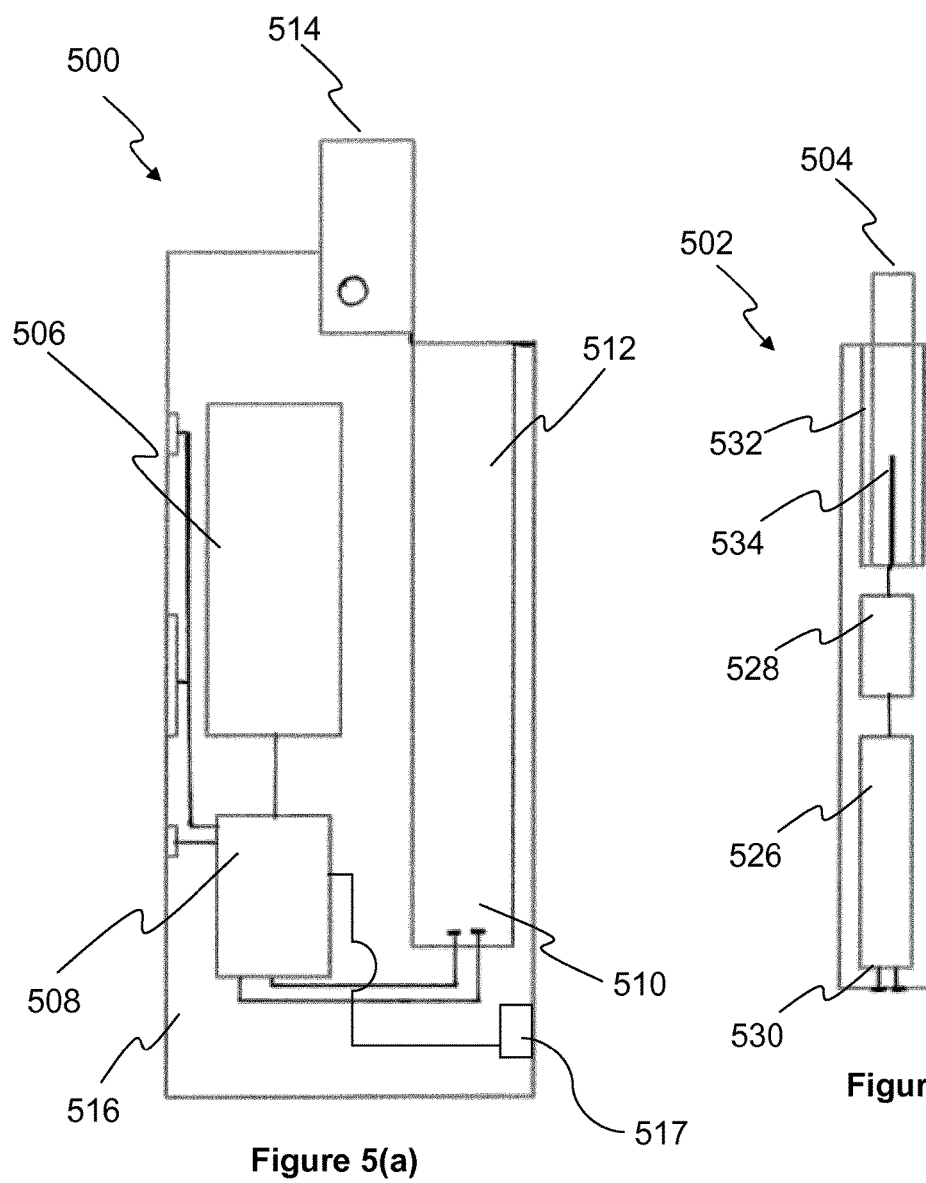
FIG. 5 shows a schematic representation of a yet further alternative aerosol-generating system according to the invention.

FIG. 5 show a yet further example of an aerosol-generating system according to the invention. FIG. 5(a) shows a charging unit 500. FIG. 5(b) shows an aerosol-generating device 502. The device 502 in this example is an electrically heated aerosol-generating device adapted to receive an aerosol-generating article 504 comprising an aerosol-forming substrate. Similarly to the article 100 described above, the article 504 also comprises a taggant. The charging device 500 comprises a primary battery 506, control electronics 508, and electrical contacts 510 configured to provide electrical power to the aerosol-generating device 502, from the battery 506, when the device 502 is in connection with the electrical contacts 510. The charging device is configured to charge the device 502 utilising the battery 506. The electrical contacts 510 are provided adjacent the bottom of a cavity 512. The cavity is configured to receive the device 502. A lid 514 is provided that is configured to secure the device 502 within the cavity 512 of the primary device 500. The components of the charging device 500 are housed within the housing 516.

The charging unit 500 is further provided with a detector 517, similar to the detector described above, on an external surface of the housing 516.

The device 502 comprises a rechargeable battery 526, secondary control electronics 528 and electrical contacts 530. As described above, the rechargeable battery 526 of the device 502 is configured to receive a supply of power from the primary battery 506 when the electrical contacts 530 are in contact with the electrical contacts 510 of the charging device 500 and the lid is in the closed position. The device 502 further comprises a cavity 532 configured to receive the aerosol generating article 504. A heater 534, in the form of, for example, a blade heater, is provided at the bottom of the cavity 532.

In use, with the device 502 within the cavity 512 of the charging unit, the user activates the device 502 by presenting an article 504 to the detector 517 on the charging unit. If the article is recognised as an article configured for use in the system, the control electronics 508 sends a signal to the device 502 which enables the device for use. Power may then be provided from the battery 526 via the control electronics 528 to the heater 534. The heater is heated to a standard operational temperature that is sufficient to generate an aerosol from the aerosol-forming substrate of the aerosol-generating article 504.

In one example, the lid 514 comprises a locking mechanism to retain the device 502 within the cavity 512 until an article 504, which is configured for use with the system, is presented to the detector 517.

Figure 6A:
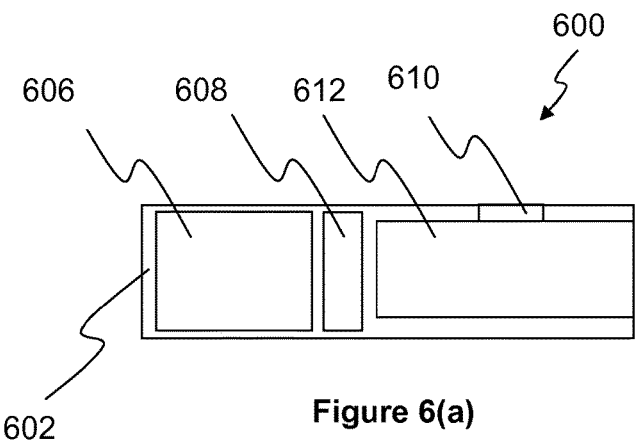
FIG. 6 show schematic representations of another alternative aerosol-generating system according to the invention.
Figure 6B:
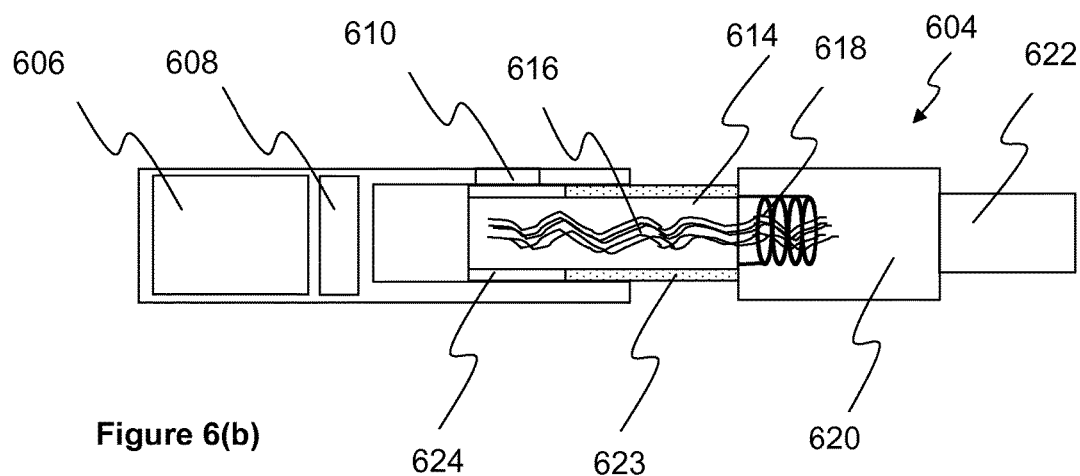
Figure 6C:
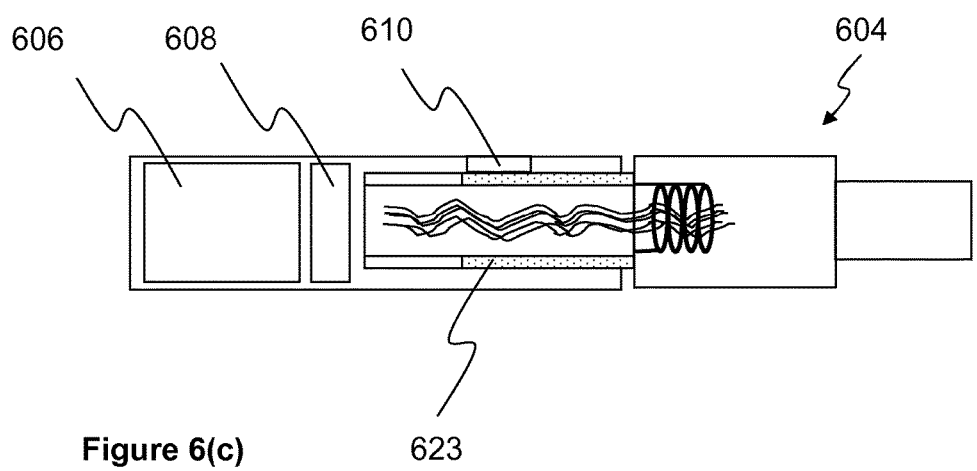

FIG. 6 show schematic representations of a further exemplary embodiment of an aerosol-generating system 600 according to the invention. The system of FIG. 6 is similar to that shown in FIG. 3. The aerosol-generating system 600 comprises an aerosol-generating device 602 and an aerosol-generating article 604. The aerosol-generating device 602 comprises a power supply 606, such as a battery, control circuitry 608, and a detector 610. The device 302 is also provided with a cavity 612 for receiving the aerosol-generating article 604. The aerosol-generating article 604 comprises an aerosol-generating liquid substrate container 614, a capillary wick 616, an electrically operated heater 618, an aerosol forming chamber 620 and a mouthpiece 622.

The aerosol-generating article 604 is a cartridge, such as a disposable cartridge, for use in the aerosol-generating device 602. The container of the cartridge comprises a taggant 623, as described herein, incorporated into the material used to form the container. The taggant has an identifiable spectroscopic signature. A portion 624 of the container, receivable in the cavity 612 of the device 602 does not comprise a taggant. However, as will be appreciated, the taggant may be provided throughout the container, in a similar way to articles 100, 304 and 504 described above.

Similarly to the exemplary embodiment shown in FIGS. 2 and 3, the detector 610 is capable of detecting the presence of the aerosol-generating article 604 in the cavity and distinguishing the aerosol-generating article from other articles configured for use with the aerosol-generating system 600, based on the taggant incorporated within the material of the container. The detector 610 comprises a light source and a light sensor for determining the spectroscopic signature of the taggant to identify the aerosol-generating article 604.

In use, the device 602 is initially in a first, low power, mode in which the detector monitors only for the presence of an aerosol-generating article. In the first mode, the detector is not capable of determining the spectroscopic signature of the taggant. In one example, the power consumption of the device in the first mode is about 5 mA. The device 602 in the first mode, awaiting the user to insert an aerosol-generating article into the cavity is shown in FIG. 6(*a*).

As shown in FIG. 6(*b*), when the user inserts an aerosol-generating article 604 into the cavity 612, the detector detects the presence of the article, and the electrical hardware switches the device to operate in a second mode, in which the detector is capable of determining the spectroscopic signature of the taggant. In the first mode, the detector emits light, at a low power, and monitors a light sensor for the received signal. When the received light exceeds a pre-determined threshold, the detector determines that an aerosol-generating article is present.

In one example, when in the second mode, the detector has a power consumption of about 8 mA.

On continued insertion into the cavity, as shown in FIG. 6(*c*), the taggant containing portion of the article 604 is provided adjacent the detector 610. The device 602 is in the second mode of operation and is capable of determining the taggant, and comparing the determined taggant to a list of taggants corresponding to articles for use with the system. The operation of the device then continues as described above.

The detector and associated electrical hardware described with reference to FIG. 6 may also be employed in the systems 200, 400 and 500 described with reference to FIGS. 2, 4 and 5 respectively. That is to say, the systems 200, 400 and 500 may be provided with a detector, or device, capable of operating in a first mode in which the detector is only configured to detect the presence of an aerosol-generating article, and in a second mode in which the spectroscopic signature of a taggant can be determined.

The exemplary embodiments described above illustrate but are not limiting. In view of the above-discussed exemplary embodiments, other embodiments consistent with the above exemplary embodiments will now be apparent to one of ordinary skill in the art.

The invention claimed is:

1. A method of controlling an aerosol-generating system, the system comprising:
    an aerosol-generating article including an aerosol-forming substrate and at least one component incorporating a taggant having an identifiable spectroscopic signature within a material of the at least one component; and
    an aerosol-generating device, comprising:
        a cavity configured to at least partially receive the aerosol-generating article;
        a power supply configured to supply power to at least one heating element to heat the aerosol-forming substrate to form an aerosol;
        control circuitry connected to the power supply; and
        a detector configured to detect the presence of the aerosol-generating article and to detect the identifiable spectroscopic signature of the taggant;
        wherein the control circuitry is configured to distinguish the aerosol-generating article from other articles configured for use with the aerosol-generating system, based on the spectroscopic signature detected by the detector, and
        wherein the taggant is distributed throughout the material,
    the method comprising:
        detecting, by the detector, a presence of the aerosol-generating article;
        determining, by the control circuitry, whether the aerosol-generating article comprises the taggant;
        comparing, by the control circuitry, the spectroscopic signature of a detected taggant with a look-up table of taggant spectroscopic signatures corresponding to aerosol-generating articles configured for use with the aerosol-generating system;
        preventing, by the control circuitry, activation of the aerosol-generating device, including preventing the supply of power to the at least one heating element, unless the detected taggant spectroscopic signature corresponds to the aerosol-generating article configured for use with the aerosol-generating system; and
        activating, by the control circuitry, the aerosol-generating device if the detected taggant spectroscopic signature corresponds to the aerosol-generating article configured for use with the aerosol-generating system.

2. The method of controlling an aerosol-generating system according to claim 1, further comprising detecting a presence of the aerosol-generating article presented externally to the aerosol-generating device.

3. The method of controlling an aerosol-generating system according to claim 2, wherein the preventing activation of the aerosol-generating device further includes preventing the aerosol-generating article from being received in the cavity of the aerosol-generating device.

4. The method of controlling an aerosol-generating system according to claim 1,
    wherein the aerosol-generating system further comprises a charging unit configured to charge the power supply, and
    wherein the method further comprises:
        detecting a presence of the aerosol-generating article presented externally to the charging unit; and
        providing an activation signal from the charging unit to the aerosol-generating device unless the detected taggant spectroscopic signature corresponds to the aerosol-generating article configured for use with the aerosol-generating system.

5. The method of controlling an aerosol-generating system according to claim 4,
    wherein the charging unit further comprises a cavity configured to at least partially receive the aerosol-generating device, and
    wherein the method further comprises preventing release of the aerosol-generating device from the charging unit unless the detected taggant spectroscopic signature corresponds to the aerosol-generating article configured for use with the aerosol-generating system.

6. The method of controlling an aerosol-generating system according to claim 1, further comprising increasing the temperature of the at least one heating element to above a temperature at which the taggant is deactivated, preventing the aerosol-generating article from being used again.

7. The method of controlling an aerosol-generating system according to claim 6, further comprising detecting an end of life of the aerosol-generating article, and increasing the temperature in dependence on the aerosol-generating article having reached the end of life.

8. The method of controlling an aerosol-generating system according to claim 1, the method further comprising:
in a first mode of operation, detecting the presence of the aerosol-generating article and switching to a second mode of operation when the presence of an aerosol-generating article is detected; and
in the second mode of operation, determining whether the aerosol-generating article comprises a taggant and, if so, determining the spectroscopic signature of the detected taggant,
wherein in the first mode, the detector operates in a low power mode, and in the second mode, the detector operates in a high power mode.

9. The method of controlling an aerosol-generating system according to claim 8, wherein, in the first mode, the method further comprises detecting the presence of the aerosol-generating article using a proximity sensor, and in the second mode, the method further comprises determining the spectroscopic signature of the detected taggant using a light emitter and receiver.

10. An electrically operated aerosol-generating system, comprising:
an aerosol-generating article including an aerosol-forming substrate and at least one component incorporating a taggant having an identifiable spectroscopic signature within a material of the at least one component; and
an aerosol-generating device, comprising:
a cavity configured to at least partially receive the aerosol-generating article;
a power supply configured to supply power to at least one heating element to heat the aerosol-forming substrate to form an aerosol;
control circuitry connected to the power supply; and
a detector configured to detect the presence of the aerosol-generating article and to detect the identifiable spectroscopic signature of the taggant,
wherein the control circuitry is configured to distinguish the aerosol-generating article from other articles configured for use with the aerosol-generating system, based on the spectroscopic signature detected by the detector, and
wherein the taggant is distributed throughout the material.

11. The electrically operated aerosol-generating system according to claim 10, wherein the identifiable spectroscopic signature comprises absorption of a specific wavelength.

12. The electrically operated aerosol-generating system according to claim 10, wherein the identifiable spectroscopic signature comprises emission of at least one wavelength.

13. The electrically operated aerosol-generating system according to claim 12, wherein the taggant, upon excitation by light, emits the at least one wavelength, shifted from a wavelength of the excitation light.

14. The electrically operated aerosol-generating system according to claim 10, wherein the taggant is homogeneously distributed throughout the material.

15. The electrically operated aerosol-generating system according to claim 10,
wherein, between a temperature of about 50 degrees Celsius and about 500 degrees Celsius, the taggant is deactivated, and
wherein, in use, a temperature required to generate an aerosol is greater than a temperature required to deactivate the taggant.

16. The electrically operated aerosol-generating system according to claim 10, wherein the taggant is a powder composed of at least one of a rare earth metal, an actinide metal oxide, and a ceramic.

17. The electrically operated aerosol-generating system according to claim 10, wherein the detector is provided adjacent to an external surface of the aerosol-generating device.

18. The electrically operated aerosol-generating system according to claim 17,
wherein the aerosol-generating device further comprises means for preventing the aerosol-article-generating article from being received in the cavity, and
wherein the control circuitry is configured to control the preventing means to open the cavity responsive to the spectroscopic signature detected by the detector.

19. The electrically operated aerosol-generating system according to claim 10, further comprising a charging unit configured to charge the power supply, wherein the detector is provided adjacent to an external surface of the charging unit.

20. The electrically operated aerosol-generating system according to claim 19, wherein the charging unit comprises second control circuitry configured to provide an activation signal to the aerosol-generating device when the detected taggant spectroscopic signature corresponds to the aerosol-generating article configured for use with the aerosol-generating system.

21. The electrically operated aerosol-generating system according to claim 20, wherein the charging unit further comprises:
a cavity configured to at least partially receive the aerosol-generating device; and
means for preventing release of the aerosol-generating device from the charging unit unless the detected taggant spectroscopic signature corresponds to the aerosol-generating article configured for use with the aerosol-generating system.

22. The electrically operated aerosol-generating system according to claim 10, wherein the control circuitry is arranged to establish a heating protocol for the at least one heating element based on a particular aerosol-generating article distinguished by the detector.

23. The electrically operated aerosol-generating system according to claim 10, wherein the detector is a spectroscopic detector comprising an optical sensor including at least one light emitter and at least one light sensor.

24. The electrically operated aerosol-generating system according to claim 10,
wherein the detector is configured to operate in a first mode, and the detector is configured to detect the presence of the aerosol-generating article,
wherein, in a second mode, the detector is configured to determine whether the aerosol-generating article comprises a taggant and if so, to determine the spectroscopic signature of the detected taggant,
wherein the detector is further configured to switch from the first mode to the second mode when the presence of the aerosol-generating article is detected, and wherein a power consumption of the detector in the first mode is lower than a power consumption of the detector in the second mode.

25. The electrically operated aerosol-generating system according to claim 24, wherein the detector includes a proximity detector, the proximity detector being active in the first mode.

26. The electrically operated aerosol-generating system according to claim 24, wherein the control circuitry is configured to switch the detector from the first mode to the second mode when the presence of the aerosol-generating article is detected.

* * * * *